US006710079B1

(12) United States Patent
Ashmead et al.

(10) Patent No.: US 6,710,079 B1
(45) Date of Patent: *Mar. 23, 2004

(54) COMPOSITION AND METHOD FOR PREPARING AMINO ACID CHELATES AND COMPLEXES FREE OF INTERFERING COMPLEX IONS

(75) Inventors: H. DeWayne Ashmead, Fruit Heights, UT (US); Stephen D. Ashmead, Clinton, UT (US); David C. Wheelwright, Layton, UT (US); Clayton Ericson, Morgan, UT (US); Mark Pedersen, Kaysville, UT (US)

(73) Assignee: Albion International, Inc., Clearfield, UT (US)

( * ) Notice: Subject to any disclaimer, the term of this patent is extended or adjusted under 35 U.S.C. 154(b) by 578 days.

This patent is subject to a terminal disclaimer.

(21) Appl. No.: 09/686,683

(22) Filed: Oct. 11, 2000

(51) Int. Cl.$^7$ .................. A61K 31/28; C07F 3/00; C07F 11/00; C07F 13/00; C07F 15/00
(52) U.S. Cl. .................. 514/492; 556/50; 556/63; 556/116; 556/134; 556/148; 514/494; 514/499; 514/501; 514/502
(58) Field of Search .................. 556/50, 63, 116, 556/134, 148; 514/492, 494, 499, 501, 502

(56) References Cited

U.S. PATENT DOCUMENTS

| | | | |
|---|---|---|---|
| 2,877,253 A | 3/1959 | Rummel | 260/439 |
| 2,957,806 A | 10/1960 | Rummel | 167/68 |
| 2,960,406 A | 11/1960 | Cardon | 99/2 |
| 3,396,104 A | 8/1968 | Miller | 210/54 |
| 3,463,858 A | 8/1969 | Anderson | 424/289 |
| 3,775,132 A | 11/1973 | Richards, Jr. | 426/364 |
| 4,020,158 A | 4/1977 | Ashmead et al. | 424/177 |
| 4,067,994 A | 1/1978 | Anderson et al. | 424/295 |
| 4,103,003 A | 7/1978 | Ashmead | 424/177 |
| 4,167,564 A | 9/1979 | Jensen | 424/177 |
| 4,172,072 A | 10/1979 | Ashmead | 260/115 |
| 4,183,947 A | 1/1980 | Cockerill | 424/295 |
| 4,216,143 A | 8/1980 | Ashmead | 260/113 |
| 4,216,144 A | 8/1980 | Ashmead | 260/115 |
| 4,599,152 A | 7/1986 | Ashmead | 204/72 |
| 4,725,427 A | 2/1988 | Ashmead et al. | 424/44 |
| 4,774,089 A | 9/1988 | Ashmead | 424/157 |
| 4,830,716 A | 5/1989 | Ashmead | 204/72 |
| 4,863,898 A | 9/1989 | Ashmead | 514/6 |
| 5,162,369 A | 11/1992 | Ashmead et al. | 514/492 |
| 5,270,297 A | 12/1993 | Paul et al. | 514/23 |
| 5,292,538 A | 3/1994 | Paul et al. | 426/74 |
| 5,292,729 A | 3/1994 | Ashmead | 514/168 |
| 5,516,925 A | 5/1996 | Pedersen et al. | 556/50 |
| 5,596,016 A | 1/1997 | Ashmead et al. | 514/492 |
| 5,614,553 A | 3/1997 | Ashmead et al. | 514/505 |
| 6,114,379 A | 9/2000 | Wheelwright et al. | 514/492 |
| 6,159,530 A | 12/2000 | Christiansen et al. | 426/626 |
| 6,166,071 A | 12/2000 | Ashmead et al. | 514/494 |
| 6,207,204 B1 | 3/2001 | Christiansen et al. | 426/74 |
| 6,407,138 B1 * | 6/2002 | Ashmead et al. | 514/492 |
| 6,458,981 B1 * | 10/2002 | Ashmead et al. | 556/50 |

* cited by examiner

*Primary Examiner*—Porfirio Nazario-Gonzalez
(74) *Attorney, Agent, or Firm*—Thorpe North & Western, LLP

(57) ABSTRACT

A composition and method of preparing amino acid chelates and complexes free of interfering ions by blending an amino acid ligand, a calcium oxide and/or hydroxide, and a hydrated metal sulfate salt, placing the blend in a closed environment, heating the blend, and allowing the blend to react is disclosed and described. By heating at low to moderate temperatures in an enclosed environment, the waters of hydration of the metal salt are retained in the enclosed environment and serve to provide the moisture necessary to enable a bonding reaction to take place between the electron rich functional groups of the ligand and the metal ion of the hydrated metal sulfate salt. Additionally, calcium sulfate is formed which can be maintained in the final product.

40 Claims, No Drawings

COMPOSITION AND METHOD FOR PREPARING AMINO ACID CHELATES AND COMPLEXES FREE OF INTERFERING COMPLEX IONS

FIELD OF THE INVENTION

The present invention is drawn to a composition and method of preparing pure amino acid chelates. Particularly, by (a) blending hydrated metal sulfate salts, calcium hydroxides or oxides, and amino acid ligands, (b) placing the particulate blend in an enclosed environment; and (c) applying heat to the particulate blend in the enclosed environment causing the waters of hydration of the hydrated metal sulfate salt to be released into the enclosed environment, amino acid chelates and complexes are formed that are free of interfering complex ions. The waters of hydration of the hydrated sulfate salts serve to provide the moisture necessary to enable a bonding reaction to take place between the electron rich functional groups of the amino acid ligand and the metal ion of the hydrated metal sulfate salt. Further, the calcium in the calcium hydroxide or oxide is used to form the calcium sulfate which is inert and may have desirable properties if left in the final product.

BACKGROUND OF THE INVENTION

A chelate is a definite structure resulting from precise requirements of synthesis. Proper conditions must be present for chelation to take place including proper mole ratios of ligands to metal ions, pH, and solubility of reactants. As such, traditional "wet" methods of preparing chelates have typically been used to prepare chelates. These methods include the step of dissolving raw materials in solution to ionize the solution or create an appropriate electronic configuration in order for bonding to develop. Though wet methods have typically been used to make chelates, chelates and/or complexes have also been made under dry conditions.

In U.S. Pat. Nos. 2,877,253 and 2,957,806, the entire teachings of which are incorporated by reference, a ferrous sulfate-glycine complex that is substantially free from ferric iron is disclosed. By following the process of dry blending and heating the reactants as is disclosed in these patents, at least some complexing and even some may chelation occur. In fact, these patents teach that there is a distinct color change that takes place as a result of the reaction, i.e. the "complex turns uniformly light brown." However, the reactions described therein are not capable of reacting to completion. This is because a minimum amount of water is needed to drive the reaction. Because the reaction described in the patent is carried out in open air conditions, when the waters of hydration are liberated, the liberated water is released to the open atmosphere. Thus, some of the liberated water drives the reaction and some is evaporated.

The processes described in U.S. Pat. Nos. 2,877,253 and 2,957,806 have been recently improved as described in two U.S. Patent Applications filed of even date herewith entitled "A COMPOSITION AND METHOD FOR PREPARING AMINO ACID CHELATES AND COMPLEXES," and "A COMPOSITION AND METHOD FOR PREPARING GRANULAR AMINO ACID CHELATES AND COMPLEXES," the entire teachings of each are incorporated herein by reference (hereinafter referred to under Ser. Nos. 09/686,047 and 09/686,413 respectively). In those applications, the reaction is carried further (or in many cases carried to completion) because all of the reactants are retained in an enclosed environment. Specifically, by minimizing or eliminating the evaporation of water produced by the hydrated sulfate salt in the reaction blend, the waters of hydration are retained to drive the reaction further to completion than disclosed previously.

Chelation can be confirmed and differentiated from mixtures of components by infrared spectrometer analysis (hereinafter "IR"). Essentially, bond stretching and absorption caused by bond formation are analyzed by peak comparison. By utilizing IR, the complexes described in the Rummel patents show a substantial amount of free, unreacted glycine. However, the IR scans also indicate that some chelates and complexes are formed.

As applied in the field of mineral nutrition, there are a few allegedly "chelated" products which are commercially utilized. The first is referred to as a "metal proteinate." The American Association of Feed Control officials (AAFCO) has defined a "metal proteinate" as the product resulting from the chelation of a soluble salt with amino acids and/or partially hydrolyzed proteins. Such products are referred to as the specific metal proteinate, e.g., copper proteinate, zinc proteinate, etc. This definition does not contain any requirements to assure that chelation is actually present. On the basis of the chemical reactant possibilities, there are some real reservations as to the probability of chelation occurring to any great degree. For example, the inclusion of partially hydrolyzed proteins as suitable ligands and the term "and/or" in reference to such ligands implies that products made solely from partially hydrolyzed protein and soluble salts would have the same biochemical and physiological properties as products made from combining amino acids and soluble metal salts. Such an assertion is chemically incorrect. Partially hydrolyzed protein ligands may have molecular weights in the range of thousands of daltons and any bonding between such ligands and a metal ion may be nothing more than a complex or some form of ionic attraction, i.e., the metal drawn in close proximity to carboxyl moiety of such a ligand.

While some products marketed as metal proteinates during the 1960's and 1970's were true chelates, this was prior to the adoption of the AAFCO definition. An analysis of products currently marketed as metal proteinates reveals that most, if not all, are mixtures of metal salts and hydrolyzed protein or complexes between metal salts and hydrolyzed protein. Most are impure products which are difficult to analyze and are not consistent in protein make-up and/or mineral content.

The second product, referred to as an "amino acid chelate," when properly formed, is a stable product having one or more five-membered rings formed by reaction between the carboxyl oxygen, and the α-amino group of an α-amino acid with the metal ion. Such a five-membered ring is defined by the metal atom, the carboxyl oxygen, the carbonyl carbon, the α-carbon and the α-amino nitrogen. The actual structure will depend upon the ligand to metal mole ratio. The ligand to metal mole ratio is at least 1:1 and is preferably 2:1 but, in certain instances, may be 3:1 or even 4:1. Most typically, an amino acid chelate may be represented at a ligand to metal ratio of 2:1 according to Formula 1 as follows:

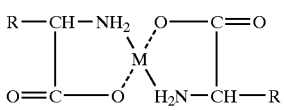

Formula 1

In the above formula, the dashed lines represent coordinate covalent bonds, covalent bonds, or ionic bonds. The solid lines between the α-amino group and the metal (M) are covalent or coordinate covalent bonds. Further, when R is H, the amino acid is glycine which is the simplest of the α-amino acids. However, R could be representative of any other of the other twenty or so naturally occurring amino acids derived from proteins. These all have the same configuration for the positioning of the carboxyl oxygen and the α-amino nitrogen. In other words, the chelate ring is defined by the same atoms in each instance.

The American Association of Feed Control Officials (AAFCO) have also issued a definition for an amino acid chelate. It is officially defined as the product resulting from the reaction of a metal ion from a soluble metal salt with amino acids with a mole ratio of one mole of metal to one to three (preferably two) moles of amino acids to form coordinate covalent bonds. The average weight of the hydrolyzed amino acids must be approximately 150 and the resulting molecular weight of the chelate must not exceed 800. The products are identified by the specific metal forming the chelate, e.g., iron amino acid chelate, copper amino acid chelate, etc.

The reason a metal atom can accept bonds over and above the oxidation state of the metal is due to the nature of chelation. In one embodiment of Formula 1, it is noted that one bond is formed from the carboxyl oxygen and the other bond is formed by the α-amino nitrogen which contributes both of the electrons used in the bonding. These electrons fill available spaces in the d-orbitals. This type of bond is known as a dative bond or a coordinate covalent bond and is common in chelation. Thus, a metal ion with a normal valency of +2 can be bonded by four bonds when fully chelated. When chelated in the manner described the divalent metal ion, the chelate is completely satisfied by the bonding electrons and the charge on the metal atom (as well as on the overall molecule) is zero. This neutrality contributes to the bioavailability of metal amino acid chelates.

The structure, chemistry and bioavailability of amino acid chelates is well documented in the literature, e.g. Ashmead et al., Chelated Mineral Nutrition, (1982), Chas. C. Thomas Publishers, Springfield, Ill.; Ashmead et al., Intestinal Absorption of Metal Ions, (1985), Chas. C. Thomas Publishers, Springfield, Ill.; Ashmead et al., Foliar Feeding of Plants with Amino Acid Chelates, (1986), Noyes Publications, Park Ridge, N.J.; U.S. Pat. Nos. 4,020,158; 4,167,564; 4,216,143; 4,216,144; 4,599,152; 4,774,089; 4,830,716; 4,863,898; and 4,725,427, the entire teachings of which are incorporated by reference.

Amino acid chelates can also be formed using small peptide ligands instead of single amino acids. These will usually be in the form of dipeptides, tripeptides and sometimes tetrapeptides because larger ligands have molecular weights that are too great for direct assimilation of the chelate formed. Generally, peptide ligands will be derived by the hydrolysis of protein. However, peptides prepared by conventional synthetic techniques or genetic engineering can also be used. When a ligand is a di- or tripeptide, a radical of the formula $[C(O)CHRNH]_e H$ will replace one of the hydrogens attached to the nitrogen atom in Formula 1. R, as defined in Formula 1, can be H, or the residue of any other naturally occurring amino acid and e can be an integer of 1, 2 or 3. When e is 1 the ligand will be a dipeptide, when e is 2 the ligand will be a tripeptide and so forth.

In the past, amino acid chelates have generally been made by first dissolving a water soluble metal salt in water. An amino acid ligand is then reacted with the metal ion at a ligand to metal molar ratio of about 1:1 to 4:1. Often, the ligand is a hydrolysis product obtained by acid, base, base-acid, base-acid-base, or enzyme hydrolysis. In such cases, the by products from hydrolysis, such as anions including chlorides, sulfates, phosphates and nitrates, and cations, including potassium and sodium remain in the hydrolysate. Reaction products of metal salts with proteins or with acid and/or base hydrolyzed proteins are taught in U.S. Pat. Nos. 2,960,406; 3,396,104; 3,463,858; 3,775,132; 4,020,158; 4,103,003, 4,172,072, the entire teachings of which are incorporated by reference.

In fact, most water soluble salts used in making amino acid chelates have been either sulfates or chlorides. Using the sulfate ion as exemplary, the reaction has generally proceeded according to Formula 2 as follows:

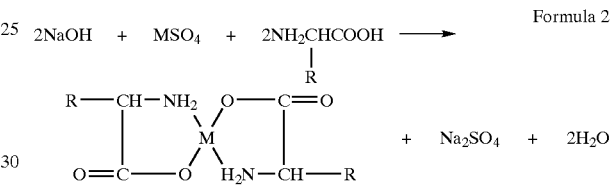

Formula 2 where M is a bivalent metal cation and R is a radical of a naturally occurring amino acid, dipeptide, or polypeptide. It is apparent from the above formula that the sulfate anion is present in the product in the form of sodium sulfate.

U.S. Pat. No. 2,877,253 teaches a product formed by the reaction of one mole of glycine with one mole of ferrous sulfate. That patent indicates that the sulfate anion becomes tied up in the reaction which allegedly forms a ferrous sulfate-glycine complex. Whether or not the sulfate actually participates in the reaction, or is present as the salt of an alkali metal, it nevertheless is present in the reaction mixture and as part of the product. Such products are difficult to purify. As sodium sulfate, per se, is water soluble, the reaction between a metal sulfate and an amino acid is never carried to 100% completion and the sulfate ion is always present. The same holds true for the presence of chloride ions when utilizing a metal chloride salt for amino acid chelate preparation.

Even if one were to attempt to wash out the excess sulfate or chloride ions with repeated washes, such an attempt could well be counter productive inasmuch as glycine and other amino acid ligands are also soluble to a degree. Hence, depending upon pH, the unreacted ligands or weakly held ligands could also be removed along with the unwanted anions.

As mentioned, in order to manufacture amino acid chelates, it generally requires that the metal salt and the ligand both be dissolved in water. One problem with this is employing metal salts that are soluble but essentially free from anions that can interfere with the chelation process. This is the subject of U.S. Pat. Nos. 4,599,152 and 4,830,716, both of which are incorporated by reference.

In the past, if certain soluble metal salts, such as sulfates, were used as a mineral source for chelation purposes, the resulting anions interfered with the chelation process. For example, the attraction between the lone pair of electrons on the amine group of an amino acid and a hydrogen ion is strong. This is why glycine is represented by the zwitterionic structure $^+H_3NCH_2COO^-$. This strong attraction for the hydrogen ion explains why amino acids are weak acids, e.g., the glycine is not easily deprotonated. In water, only about 0.5% of the glycine typically disassociates and releases a hydrogen ion.

In the prior art, the introduction of metal acid salts into solution, such as copper sulfate, resulted in the creation of copper ions which compete with the hydrogen ion for the lone pair of electrons on the $NH_2$ group. Unfortunately, the equilibrium favors the majority of the amino groups remaining protonated. Thus, in order to efficiently chelate metal ions from certain soluble salts, it becomes desirable to render the interfering anions inactive or use soluble metal salts with non-interfering anions, such as oxides or hydroxides. Thus, if a calcium hydroxide or calcium oxide is added in conjunction with a metal sulfate salt in an aqueous environment and at appropriate amounts, an amino acid chelate free of interfering ions may be formed. This is the subject of two pending U.S. patent applications filed of even date herewith entitled "A COMPOSITION AND METHOD FOR PREPARING AMINO ACID CHELATE HYDROXIDES FREE OF INTERFERING IONS," and "A COMPOSITION AND METHOD FOR PREPARING ELECTRICALLY NEUTRAL AMINO ACID CHELATES FREE OF INTERFERING IONS," both of which are incorporated herein by reference (hereinafter referred to as Ser. Nos. 09/686,046 and 09/686,684 respectively). Additionally, by preparing chelates and complexes under dry conditions, the preparation process is simplified and the product produced is generally quite stable, granular, dense, dry, and/or free flowing.

SUMMARY OF THE INVENTION

Compositions and methods of preparing amino acid chelates and complexes essentially free of interfering complex ions are disclosed which comprise a) combining as a particulate blend i) a hydrated metal sulfate salt having one or more waters of hydration, ii) an amino acid ligand, and iii) calcium oxide or hydroxide, at a ratio sufficient to allow substantially all of the particulates to react forming a metal amino acid chelate, calcium sulfate, residual water, and optionally, a hydroxide complex ion, and wherein the metal amino acid chelate has a ligand to metal molar ratio from about 1:1 to 3:1; b) placing the particulate blend in an enclosed environment; and c) applying heat to the particulate blend in the enclosed environment causing the waters of hydration of the hydrated metal sulfate salt to be released into the enclosed environment thereby causing a reaction resulting in the formation of a metal amino acid chelate or complex and calcium sulfate.

DETAILED DESCRIPTION OF THE INVENTION

Before the present invention pertaining to the preparation of amino acid chelates and complexes is disclosed and described, it is to be understood that this invention is not limited to the particular process steps and materials disclosed herein because such process steps and materials may vary somewhat. It is also to be understood that the terminology used herein is used for the purpose of describing particular embodiments only. The terms are not intended to be limiting because the scope of the present invention is intended to be limited only by the appended claims and equivalents thereof.

It must also be noted that, as used in this specification and the appended claims, the singular forms "a," "an," and "the" include plural referents unless the content clearly dictates otherwise. "Hydrated metal sulfate salt," "metal sulfate hydrate," or "metal sulfate salt having waters of hydration" includes any metal sulfate salt that h as one or more waters of hydration capable of being released during the reactions of the present invention.

"Metal" is meant to cover all metals that are generally more soluble as sulfate salts than calcium sulfate. Though calcium is a metal, for purposes of the present disclosure, calcium is excluded within this definition unless the context clearly dictates otherwise.

"Nutritionally relevant metals" include metals that are known to be needed by living organisms, particularly plants and mammals, including humans. Metals such as copper, zinc, iron, cobalt, magnesium, manganese, chromium, among others are exemplary of nutritionally relevant metals. Though calcium is generally considered to be a nutritionally relevant metal, for purposes of the present disclosure, calcium is excluded within this definition unless the context clearly dictates otherwise. This is because calcium is used to form calcium sulfate in the present invention. "Hydrate" or "n-hydrate" is meant to include any degree of hydration attached to the metal sulfate salts where n is an integer representing the number of waters of hydration, e.g., monohydrate, dihydrate, trihydrate, tetrahydrate, pentahydrate, hexahydrate, septahydrate, octahydrate, nonahydrate, etc. Typically, n is an integer of about 1 to 15.

"Amino acid chelates and complexes" is meant to include metal ions bonded to amino acid ligands forming one or more heterocyclic ring. The bonds may be coordinate covalent, covalent, and/or ionic at the carboxyl oxygen group. However, at the α-amino group, the bond is typically a covalent or coordinate covalent bond.

"Electrically neutral" refers to amino acid chelates wherein the positively charged metal ion is fully satisfied by a negative charge on the ligand attachment by bond formation, e.g., divalent metals forming 2:1 ligand to metal molar ratio amino acid chelates, or trivalent metals forming 3:1 ligand to metal molar ratio amino acid chelates.

"Complex ion" or "interfering complex ion" is meant to include any cation or anion that typically remains in a final composition as a charged group that can interfere with the formation of the chelate and/or remains in the composition to charge balance a charged amino acid chelate. Though hydroxide complex ions are charged, they are not considered to be interfering in the context of the present invention.

"Hydroxide complex ion" includes hydroxide groups that form in certain embodiments of the present invention, i.e., divalent metal amino acid chelates having a 1:1 ligand to metal molar ratio, or trivalent metal amino acid chelates having a 2:1 ligand to metal molar ratio. When these amino acid chelates are sufficiently formed as a result of liberated waters of hydration, the hydroxide complex ions will likely ionically complex with the positively charged amino acid chelates in embodiments where the amino acid chelates formed are not electrically neutral. For purposes of the present invention, hydroxide complex ions are not considered to be interfering.

"Enclosed chamber" or "enclosed environment" shall include any system or container that is capable of being substantially sealed or closed such that the waters of hydration released from a hydrate are substantially retained, thereby providing moisture to drive any reaction within the system or container.

Essentially, the compositions and methods of preparing amino acid chelates and complexes essentially free of interfering complex ions is disclosed comprising the steps of (a) combining as a particulate blend i) a hydrated metal sulfate salt having one or more waters of hydration, ii) an amino acid ligand, and iii) calcium oxide or hydroxide, at a ratio sufficient to allow substantially all of the particulates to react forming a metal amino acid chelate, calcium sulfate, water, and optionally, a hydroxide complex ion, and wherein the metal amino acid chelate has a ligand to metal molar ratio from about 1:1 to 3:1; (b) placing the particulate blend in an enclosed environment; and (c) applying heat to the particulate blend in the enclosed environment causing the waters of hydration of the hydrated metal sulfate salt to be released into the enclosed environment thereby causing a reaction resulting in the formation of a metal amino acid chelate or complex and calcium sulfate. The amino acid chelates or complexes are formed as the reaction between functional electron rich groups of the ligand and the metal ion of the metal sulfate salt is effectuated.

In the present invention, the particulate blend must be heated for a time and at a temperature sufficient to at least begin to drive the waters of hydration from the hydrated salt into the enclosed environment, though the reaction may continue to occur after the heat has been removed. This process results in particulate amino acid chelates and complexes that are stable, granular, dense, dry, and/or free flowing, though in some instances, the product must be further ground prior to packaging or using the chelates for their intended purpose. Additionally, calcium sulfate, and in some embodiments, hydroxide counter-ions or hydroxide complex ions, and/or water are produced.

Though the preferred embodiment of the invention does not include the addition of water, some moisture such as water may be added to produce a desired result, e.g., copper sulfate monohydrate may not have enough waters of hydration to drive a reaction to substantial completion. Therefore, a small amount of water may optionally be added to assist specific reactions. If water is added, the water should preferably not be added such that there is a substantial excess after the reaction has progressed to substantial completion. For example, if zinc monohydrate was used as a reactant instead of zinc pentahydrate in a formulation where zinc pentahydrate would likely drive the reaction closer to completion, 4 molar equivalents of water could be added to the blend prior to enclosing the reactants to simulate the effect of adding zinc pentahydrate. In most circumstances and in accordance with this aspect of the present invention, from about 1 to 15 molar equivalents of water can be added.

The step of enclosing the particulate blend is important because the waters of hydration must not be allowed to substantially evaporate during the reaction. This is because the waters of hydration are necessary to drive the reaction between the ligand and the metal ion of the hydrated metal sulfate salt. Therefore, a virtually sealed environment is preferred, though an enclosure that prevents substantial contact between the reaction blend and the outside atmosphere will also provide desired results. Specifically, the enclosed chamber may be a device such as a calorimeter, a plastic lined container, a tank, a blender, a kettle, a sealed drum, or a plastic bag capable of being enclosed or sealed. However, other enclosed chambers, environments, or systems are within the scope of the invention.

Generally, time and temperature variables should be considered when determining whether the reaction has been driven forward adequately. A typical temperature range for the reaction is from about 50° C. to 100° C., though functional temperatures outside of this range may be used. In one embodiment, the particulate blend in the enclosed chamber may be heated to from 60° C. to 80° C. for from 2 to 4 hours. After, heating the particulate blend, the resulting product should be allowed to 20 cool to room temperature. In other embodiments, heating may be for periods of about 15 minutes at temperatures from about 75° C. to 85° C. The heating time and temperature as well as the cooling time and temperature will depend largely upon what metal salts, ligands, ratios, batch sizes, etc., are selected.

In order for the reaction to be driven adequately, the hydrated metal sulfate salt must have at least one water molecule available for release to catalyze the reaction. However, if for example, a metal sulfate monohydrate is used, the reaction will not advance as far as other, more hydrated, metal salts. Conversely, hydrated metal sulfate salts such as a metal sulfate pentahydrate or heptahydrate (or even higher) are preferred compounds because of the number of water molecules available for liberation during the reaction. For example, ferrous sulfate heptahydrate is one of many preferred salts to utilize as will be exemplified below.

Since the ligands of the present invention are generally amino acids, the naturally occurring amino acids including alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine, valine, and combinations thereof are preferred. However, ligands including dipeptides, tripeptides, and tetrapeptides formed by any combination of the aforementioned amino acids may also be used.

If the ligand and/or hydrated metal sulfate salts are in something other than powder form, e.g. larger crystals, etc., an additional step of grinding the raw materials into powder may be desired to increase surface area. As such, course form of hydrated metal salts and ligands should be ground in to a maximum particle size of 80 mesh.

There are certain advantages to producing amino acid chelates and complexes as described above. As mentioned previously, the waters of hydration are maintained within the closed system and are used to drive the reaction forward. The enclosed chamber serves an important function. Granules (usually crystals) are allowed to form under these conditions. After sufficient reaction time, the particulate blend often changes in color and texture. Hydrated granules form that are free-flowing and generally range in size from 30 to 80 mesh. Further, while cooling, the reaction continues to progress slowly until a dry, but hydrated, granule product forms, leaving a stable, dense, dry, and free flowing product. In some instances, the product can be further ground prior to packaging or using for its intended purpose. The reaction time may be very short or may require multiple days, depending on the embodiment. Further, the presence of calcium sulfate (terra alba) mixed in with the amino acid chelate potentially increases the ultimate bulk density of the chelate product.

By matching the valency of the desired metal ion to be used with the number of amino acid ligands to be bonded to the metal ion, the product produced is not only free of interfering complex ions, but may also be electrically neutral. For example, if ferrous iron ($Fe^{2+}$) is used to prepare amino acid chelates having a ligand to metal molar ratio of about 2:1, the final product will be free of interfering complex ions and will be electrically neutral. However, if chromium ($Cr^{3+}$) is used to prepare amino acid chelates having a ligand to metal molar ratio of 2:1, then the interfering complex ions will be free of interfering complex ions as defined herein, but the chelate itself will not be electrically neutral. However, the entire composition is charge balanced by the presence of hydroxide complex ions which act as counter ions to the positively charged amino acid chelates.

The reactions used to prepare electrically neutral amino acid chelates essentially free of interfering anions and having a ligand to metal molar ratio from about 2:1 to 3:1 are shown in Formulas 3a, 3b, 4a, and 4b below. Formulas 3a and 3b illustrate the production an electrically neutral composition comprised of calcium sulfate and amino acid chelates having a 2:1 ligand to metal molar ratio:

$$Ca(OH)_2 + 2H(AA) + MSO_4 \cdot nH_2O \rightarrow$$

$$M(AA)_2 + CaSO_4 + (n+2)H_2O \quad \text{Formula 3a}$$

$$CaO + 2H(AA) + MSO_4 \cdot nH_2O \rightarrow$$

$$M(AA)_2 + CaSO_4 + (n+1)H_2O \quad \text{Formula 3b}$$

In Formulas 3a and 3b above, H(AA) is an amino acid selected from the group consisting of naturally occurring amino acids and combinations thereof. H, when disassociated from AA, is a hydrogen ion donor from the carboxyl group present on the amino acid. M is a nutritionally relevant metal having a valency of +2 such as Cu, Zn, Fe, Co, Mg, and/or Mn, and n is an integer from about 1 to 15 that is indicative of the waters of hydration of the metal sulfate.

Formulas 4a and 4b illustrate the production an electrically neutral composition comprised of calcium sulfate and amino acid chelates having a 3:1 ligand to metal molar ratio:

$$3Ca(OH)_2 + 6H(AA) + M'_2(SO_4)_3 \cdot nH_2O \rightarrow$$

$$2M'(AA)_3 + 3CaSO_4 + (n+6)H_2O \quad \text{Formula 4a}$$

$$3CaO + 6H(AA) + M'_2(SO_4)_3 \cdot nH_2O \rightarrow$$

$$2M'(AA)_3 + 3CaSO_4 + (n+3)H_2O \quad \text{Formula 4b}$$

In Formulas 4a and 4b, H(AA) is an amino acid selected from the group consisting of naturally occurring amino acids and combinations thereof. H, when disassociated from AA, is a hydrogen ion donor from the carboxyl group present on the amino acid. M' is a nutritionally relevant metal having a valence of +3 such as Fe(III) and/or Cr, and n is an integer from about 1 to 15.

The reactions used to prepare amino acid chelates that essentially free of interfering anions and having a ligand to metal molar ratio from about 1:1 to 2:1 are shown in Formulas 5a, 5b, 6a, and 6b below. These reactions do not produce electrically neutral products due to the presence of a positive charge on the metal ion and the counter negative charge on the hydroxide ions or hydroxide complex ions. Formulas 5a and 5b illustrate the production of charge balanced but non-electrically neutral compositions free of interfering complex ions comprised of calcium sulfate, hydroxide complex ions, and amino acid chelates having a 1:1 ligand to metal molar ratio:

$$Ca(OH)_2 + H(AA) + MSO_4 \cdot nH_2O \rightarrow$$

$$M(AA)^+OH^- + CaSO_4 + (n+1)H_2O \quad \text{Formula 5a}$$

$$CaO + H(AA) + MSO_4 \cdot nH_2O \rightarrow$$

$$M(AA)^+OH^- + CaSO_4 + nH_2O \quad \text{Formula 5b}$$

In Formulas 5a and 5b above, H(AA) is an amino acid selected from the group consisting of naturally occurring amino acids and combinations thereof. H, when disassociated from AA, is a hydrogen ion donor from the carboxyl group present on the amino acid. M is a nutritionally relevant metal having a valency of +2 such as Cu, Zn, Fe, Co, Mg, and/or Mn, and n is an integer from about 1 to 15 that is indicative of the waters of hydration of the metal sulfate.

Formulas 6a and 6b illustrate the production non-electrically neutral compositions free of interfering complex ions comprised of calcium sulfate, hydroxide complex ions, and amino acid chelates having a 2:1 ligand to metal molar ratio:

$$3Ca(OH)_2 + 4H(AA) + M'_2(SO_4)_3 \cdot nH_2O \rightarrow$$

$$2[M'(AA)_2{}^+OH^-] + 3CaSO_4 + (n+2)H_2O \quad \text{Formula 6a}$$

$$3CaO + 4H(AA) + M'_2(SO_4)_3 \cdot nH_2O \rightarrow$$

$$M(AA)_2{}^+OH^- + CaSO_4 + nH_2O \quad \text{Formula 5b}$$

$$2[M'(AA)_2{}^+OH^-] + 3CaSO_4 + (n+1)H_2O \quad \text{Formula 6b}$$

In Formulas 6a and 6b, H(AA) is an amino acid selected from the group consisting of naturally occurring amino acids and combinations thereof. H, when disassociated from AA, is a hydrogen ion donor from the carboxyl group present on the amino acid. M' is a nutritionally relevant metal having a valence of +3 such as Fe(III) and/or Cr, and n is an integer from about 1 to that is indicative of the waters of hydration of the metal sulfate.

For purposes of the present invention, multiple metals, amino acids, salts, etc., may be used as well. It is important to note that the compositions and methods of the present invention always produce amino acid chelates that are free of interfering anions and also produced calcium sulfate which is largely insoluble and essentially inert. As such, the calcium sulfate preferably remains in the compound as a stabilizer or for other purposes.

Amino acid chelates and complexes of the present invention have many possible applications. They may be used as plant foliars and foods. Either the product can be dissolved for use on leaves, etc., or used directly as a soil treatment. The product can be dry blended in combination with other metal salts and/or a variety of ligands for more unique applications. These chelates and complexes can also be used in animal feeds by methods currently known in the art. In fact, some processes may create products that can be used in food applications, in pharmaceuticals, and/or nutritional supplements for warm-blooded animals, including humans.

EXAMPLES

The following examples illustrate compositions and methods of preparing the amino acid chelates and complexes of the present invention. The following examples should not be considered as limitations of the present invention, but should merely teach how to make the best known amino acid chelates and complexes based upon current experimental data.

In the present examples, theoretical values for final weight percentage are given rather than actual values. This has been done because it is difficult to determine an actual amount of water that remains in the compounds described below. In other words, since standard moisture tests would give artificially low moisture values, theoretical values have been assigned to the compositions for clarity. Additionally, all ratios when referring to amino acid chelate products are molar ratios.

Example 1

One mole of ferrous sulfate heptahydrate powder, one mole of glycine powder, and one mole of calcium oxide powder were dry blended and placed in a bomb calorimeter. The calorimeter was then submersed in a warm water bath that was maintained at about 70° C. After 15 minutes, the contents of the calorimeter began to be exothermic. The warm water in the bath was then replaced by cool tap water. Though cool water was present in the bath, the temperature of the reactants in the calorimeter remained in the temperature range from about 75° C. to 85° C. Once the reaction mixture dropped below 70° C., the reaction was near completion. The contents of the calorimeter were allowed to cool to room temperature prior to opening. Once opened, the product was then allowed to stand overnight.

The reaction produced about one mole of a 1:1 iron glycine chelate hydroxide ion complex and about one mole of calcium sulfate. By weight, the product contained about 19.9% iron and 5.5% moisture.

Example 2

One mole of copper sulfate pentahydrate powder, one mole of L-lysine powder, and one mole of calcium oxide were dry blended and placed in a bomb calorimeter. The calorimeter was then submersed in a 70° C. warm water bath. After a few minutes, the contents of the calorimeter began to be exothermic. To maintain the temperature of the reactants at about 75° C. to 85° C., the warm water in the bath was replaced by cool tap water. When the temperature of the reaction mixture fell below about 70° C., the calorimeter was removed from the cool water bath and allowed to adjust to room temperature. The calorimeter was then opened and the product was allowed to sit overnight.

The reaction produced about one mole of a 1:1 copper L-lysine chelate hydroxide ion complex and about one mole of calcium sulfate. The product produced contained about 17.2% copper and 5.2% moisture by weight.

Example 3

One mole of zinc sulfate pentahydrate powder, one mole of manganese sulfate pentahydrate powder, two moles of glycine powder, and two moles of calcium oxide were dry blended and placed in a bomb calorimeter. The calorimeter was then submersed in a warm water bath that was maintained at about 70° C. Once the contents of the calorimeter began to be exothermic, the warm water in the bath was replaced by cool tap water. The temperature of the reactants in the calorimeter remained in the temperature range from about 75° C. to 85° C. due to the contact with the cool water on the surface of the calorimeter. When the reaction mixture dropped below 70° C., the contents of the calorimeter were allowed to cool to room temperature.

After opening the calorimeter and allowing the product to stand overnight, about one mole of a 1:1 zinc glycine chelate hydroxide ion complex, about one mole of a 1:1 manganese glycine chelate hydroxide ion complex, and about two moles of calcium sulfate remained. The final product contained about 13.3% zinc, 11.2% manganese, and 4.9% moisture by weight.

Example 4

One mole of magnesium sulfate nonahydrate powder, one half mole of glycine powder, one half mole of L-methionine powder, and one mole of calcium oxide were dry blended and placed in a bomb calorimeter. The calorimeter was then submersed in a warm water bath that was maintained at about 70° C. After 15 minutes, the contents of the calorimeter began to be exothermic. The warm water in the bath was then replaced by cool tap water. Though cool water was present in the bath, the temperature of the reactants in the calorimeter remained in the temperature range from about 75° C. to 85° C. Once the reaction mixture dropped below 70° C., the reaction was near completion. The contents of the calorimeter were allowed to cool to room temperature. At this point, the calorimeter was opened and the product was allowed to stand overnight.

The reaction produced about one half mole of a 1:1 magnesium glycine chelate hydroxide ion complex, about one half mole of a 1:1 magnesium L-methionine chelate hydroxide ion complex, and about one mole of calcium sulfate. By weight, the product contained about 8.4% magnesium and 5.5% moisture.

Example 5

One mole of zinc sulfate pentahydrate powder, one mole of manganese sulfate pentahydrate powder, one mole of copper sulfate pentahydrate powder, one mole of glycine powder, one mole of L-lysine powder, one mole of L-histidine powder, and three moles of calcium oxide were dry blended and placed in a bomb calorimeter. The calorimeter was heated in a warm water bath which was maintained at about 70° C. After 15 minutes, the contents of the calorimeter began to be exothermic and the warm water in the bath was then replaced by cool tap water so that the contents would remain at from about 75° C. to 85° C. Once the reaction mixture dropped below 70° C., the reaction was near completion and the calorimeter was removed from to cool bath. After the contents had cooled to room temperature, the calorimeter was opened the product was allowed to stand overnight.

The reaction produced about three moles of amino acid chelate hydroxide ion complexes having a 1:1 ligand to metal molar ratio. All combinations were present, i.e., all combinations of zinc, manganese, and copper chelated to glycine, L-lysine, and L-histidine. The reaction also produced about three moles of calcium sulfate. By weight, the product contained about 6.4% zinc, 5.4% manganese, 6.2% copper, and 5.1% moisture.

Example 6

One mole of ferrous sulfate heptahydrate powder, one mole of glycine powder, and one mole of calcium hydroxide powder were dry blended and placed in a bomb calorimeter. The calorimeter was then submersed in a warm water bath that was maintained at about 70° C. After a few minutes, the contents of the calorimeter began to be exothermic. The warm water in the bath was then replaced by cool tap water. Though cool water was present in the bath, the temperature of the reactants in the calorimeter remained within a temperature range from about 75° C. to 85° C. Once the reaction mixture dropped below 70° C., the reaction neared completion. The contents of the calorimeter were allowed to cool to room temperature. At this point, the calorimeter was opened and the product was allowed to stand overnight.

The reaction produced about one mole of a 1:1 iron glycine chelate hydroxide ion complex and about one mole of calcium sulfate. By weight, the product contained about 18.5% iron and 5.98% moisture.

Example 7

One mole of ferrous sulfate heptahydrate powder, two moles of glycine powder, and one mole of calcium oxide powder were dry blended and placed in a bomb calorimeter. The calorimeter was then submersed in a warm water bath maintained at about 70° C. When the contents of the calorimeter began to be exothermic, the warm water in the bath was then replaced by cool tap water so that the temperature range could be maintained between about 75° C. to 85° C. At a point near completion of the reaction, the temperature of the reaction mixture dropped below 70° C. and the cool water was removed. The contents of the calorimeter were then allowed to cool to room temperature prior to opening of the calorimeter.

The product was allowed to stand overnight. About one mole ferrous bisglycinate and about one mole of calcium sulfate was formed. By weight, the product contained about 15.5% iron and 5.1% moisture.

Example 8

One mole of copper sulfate pentahydrate powder, two moles of L-lysine powder, and one mole of calcium oxide were dry blended and placed in a bomb calorimeter which was subsequently submersed in a 70° C. warm water bath. The contents of the calorimeter began to be exothermic after about 15 minutes. The warm water in the bath was then replaced by cool tap water. Though cool water was present in the bath, the temperature of the reactants in the calorimeter remained in the temperature range from about 75° C. to 85° C. Once the temperature of the reaction mixture dropped below 70° C., the calorimeter was removed from the cool water where the contents were allowed to cool to room temperature. At this point, the calorimeter was opened and the product was allowed to stand overnight.

The reaction produced about one mole of copper bisglycinate and about one mole of calcium sulfate. The product contained about 12.09% copper and 5.8% moisture by weight.

Example 9

One mole of zinc sulfate pentahydrate powder, one mole of manganese sulfate pentahydrate powder, four moles of glycine powder, and two moles of calcium oxide were dry blended and placed in a bomb calorimeter. The calorimeter was then submersed in a warm water bath that was maintained at about 70° C. After 15 minutes, the contents of the calorimeter began to be exothermic. The warm water in the bath was then replaced by cool tap water. Though cool water was present in the bath, the temperature of the reactants in the calorimeter remained in the temperature range from about 75° C. to 85° C. Once the temperature of the reaction mixture dropped below 70° C. the reaction neared completion. The contents of the calorimeter were allowed to cool to room temperature. The calorimeter was then opened and the product was allowed to stand overnight.

The reaction produced about one mole of zinc bisglycinate, about one mole of manganese bisglycinate, and about two moles of calcium sulfate. By weight, the product contained about 7.9% zinc, 9.4% manganese, and 4.9% moisture.

Example 10

One mole of magnesium sulfate nonahydrate powder, one mole of glycine powder, one mole of L-methionine powder, and one mole of calcium oxide were dry blended and placed in a bomb calorimeter. The calorimeter was then warmed and maintained at about 70° C. in a water bath. Once the reactants became exothermic, the warm water in the bath was then replaced by cool water so that the reactants in the calorimeter remained in the temperature range from about 75° C. to 85° C. Once the temperature of the reaction mixture dropped below 70° C., the calorimeter was removed from the water bath, the contents were allowed to cool to room temperature, the calorimeter was opened, and the product was allowed to stand overnight.

The reaction produced about one mole magnesium biglycinate, about one mole of magnesium bismethionate, and about one mole of calcium sulfate. The product contained about 6.2% magnesium and 5.3% moisture by weight.

Example 11

One mole of zinc sulfate pentahydrate powder, one mole of manganese sulfate pentahydrate powder, one mole of copper sulfate pentahydrate powder, two moles of glycine powder, two moles of L-lysine base powder, two moles of L-histidine powder, and three moles of calcium oxide were dry blended and placed in a bomb calorimeter. The calorimeter was then submersed in a warm water bath that was maintained at about 70° C. After 15 minutes, the contents of the calorimeter began to be exothermic. The warm water in the bath was then replaced by cool tap water. Though cool water was present in the bath, the temperature of the reactants in the calorimeter remained in the temperature range from about 75° C. to 85° C. Once the temperature of the reaction mixture dropped below 70° C., the reaction was near completion. The contents of the calorimeter were allowed to cool to room temperature. At this point, the calorimeter was opened and the product was allowed to stand overnight.

The reaction produced about three moles of amino acid chelates having a 2:1 ligand to metal molar ratio. All combinations were present, i.e., all combinations of zinc, manganese, and copper chelated to glycine, L-lysine, and L-histidine. The reaction also produced about three moles of calcium sulfate. The product contained about 4.1% zinc, 3.4% 20 manganese, 4.0% copper, and 5.0% moisture by weight.

Example 12

One mole of ferrous sulfate heptahydrate powder, two moles of glycine powder, and one mole of calcium hydroxide powder were dry blended and placed in a bomb calorimeter and submersed in a warm water bath maintained at about 70° C. Within a few minutes, the contents of the calorimeter began to be exothermic. The warm water in the bath was then replaced by cool tap water to maintain the temperature of the reactants in the calorimeter at about 75° C. to 85° C. Once the temperature of the reaction mixture dropped below 70° C., the contents of the calorimeter were allowed to cool to room temperature. After cooling, the calorimeter was opened and the product was allowed to stand overnight.

The reaction produced about one mole ferrous bisglycinate and about one mole of calcium sulfate. By weight, the product contained about 14% iron and 10% moisture.

Example 13

One half mole of chromium (III) sulfate heptahydrate powder, two moles of glycine powder, and one and one half moles of calcium oxide powder were dry blended and placed in a bomb calorimeter. The calorimeter was heated in a 70° C. warm water bath until the contents of the calorimeter began to be exothermic. The warm water in the bath was then replaced by cool tap water in order to maintain the temperature range from about 75° C. to 85° C. Once the temperature of the reaction mixture dropped below 70° C., the reaction was near completion and the contents of the calorimeter were allowed to cool to room temperature. At this point, the calorimeter was opened and the product was allowed to stand overnight.

The reaction produced about one mole of chromium bisglycinate hydroxide ion complex and about.one and one half moles of calcium sulfate. The product contained about 11.0% chromium and about 13% moisture by weight.

Example 14

One half mole of ferric iron sulfate n-hydrate powder (where n can be a mixture of compounds having from about 1 to 15 waters of hydration), two moles of glycine powder, and one and one half moles of calcium hydroxide powder were dry blended and placed in a bomb calorimeter. The calorimeter was then submersed in a warm water bath that was maintained at about 70° C. After a few minutes, the contents of the calorimeter began to be exothermic. The warm water in the bath was then replaced by cool tap water. Though cool water was present in the bath, the temperature of the reactants in the calorimeter remained in the temperature range from about 75° C. to 85° C. Once the temperature of the reaction mixture dropped below 70° C., the reaction neared completion. The contents of the calorimeter were allowed to cool to room temperature. The calorimeter was then opened and the product was allowed to stand overnight.

The reaction produced about one mole of ferric bisglycinate hydroxide ion complex and one and one half moles of calcium sulfate. By weight, the product contained about 11% iron and 13% moisture.

Example 15

One mole of chromium (III) sulfate heptahydrate powder, six moles of glycine powder, and three moles of calcium oxide powder were dry blended and placed in a bomb calorimeter. The calorimeter was then submersed in a warm water bath that was maintained at about 70° C. Once the contents of the calorimeter began to be exothermic, the warm water in the bath was then replaced by cool water in order to maintain the temperature range from about 75° C. to 85° C. When the temperature of the reaction mixture dropped below 70° C., the reaction was near completion. The contents of the calorimeter were allowed to cool to room temperature, the calorimeter was opened, and the product was allowed to stand overnight.

The reaction produced about two moles of chromium trisglycinate and about three moles of calcium sulfate. By weight, the product contained about 10% chromium and 9% moisture.

Example 16

One mole of chromium (III) sulfate heptahydrate powder, six moles of glycine powder, and three moles of calcium hydroxide powder were dry blended and placed in a bomb calorimeter. The calorimeter was then submersed in a warm water bath that was maintained at about 70° C. After 15 minutes, the contents of the calorimeter began to be exothermic. The warm water in the bath was then replaced by cool tap water. Though cool water was present in the bath, the temperature of the reactants in the calorimeter remained in the temperature range from about 75° C. to 85° C. Once the temperature of the reaction mixture dropped below 70° C., the reaction was near completion. The contents of the calorimeter were allowed to cool to room temperature. At this point, the calorimeter was opened and the product was allowed to stand overnight.

The reaction produced about two moles of chromium trisglycinate and about three moles of calcium sulfate. By weight, the product contained about 10% chromium and 9% moisture.

While the invention has been described with reference to certain preferred embodiments, those skilled in the art will appreciate that various modifications, changes, omissions, and substitutions can be made without departing from the spirit of the invention. It is intended, therefore, that the invention be limited only by the scope of the following claims.

We claim:

1. A method of preparing amino acid chelates and complexes essentially free of interfering complex ions comprising the steps of:
    a) combining as a particulate blend
        i) a hydrated metal sulfate salt having one or more waters of hydration,
        ii) an amino acid ligand, and
        iii) calcium oxide or hydroxide,
    at a ratio sufficient to allow substantially all of the particulates to react forming a metal amino acid chelate, calcium sulfate, residual water, and optionally, a hydroxide complex ion, and wherein the metal amino acid chelate has a ligand to metal molar ratio from about 1:1 to 3:1;
    b) placing the particulate blend in an enclosed environment; and
    c) applying heat to the particulate blend in the enclosed environment causing the waters of hydration of the hydrated metal sulfate salt to be released into the enclosed environment thereby causing a reaction resulting in the formation of a metal amino acid chelate or complex and calcium sulfate.

2. A method as in claim 1 wherein said amino acid ligand is selected from the group consisting of alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine, valine, and combinations thereof, and dipeptides, tripeptides, and tetrapeptides formed by any combination of said amino acids thereof.

3. A method as in claim 1 wherein said metal sulfate salt is selected from the group consisting of iron sulfate hydrates, copper sulfate hydrates, zinc sulfate hydrates, manganese sulfate hydrates, cobalt sulfate hydrates, magnesium sulfate hydrates, chromium sulfate hydrates, molybdenum sulfate hydrates, and combinations thereof.

4. A method as in claim 1 wherein the particulate blend within the enclosed environment is heated at temperatures from about 50° C. to 100° C.

5. A method as in claim 1 wherein following the heating step, the temperature of the particulate blend is reduced to room temperature and allowed to continue to react.

6. A method as in claim 2 wherein the amino acid ligand is glycine.

7. A method as in claim 2 wherein the amino acid ligand is comprised of glycine and at least one of the other naturally occurring amino acids.

8. A method as in claim 3 wherein the hydrated metal sulfate salt is selected from the group consisting of ferrous sulfate tetrahydrate, ferrous sulfate heptahydrate, copper sulfate pentahydrate, manganese sulfate pentahydrate, zinc sulfate pentahydrate, magnesium sulfate nonahydrate, chromium sulfate heptahydrate, zinc sulfate monohydrate, and combinations thereof.

9. A method as in claim 1 further comprising a preliminary step of grinding said ligand and said hydrated metal sulfate salt into a powder from about 20 to 80 mesh.

10. A method as in claim 1 wherein the amino acid chelate formed is electrically neutral.

11. A method as in claim 1 wherein the amino acid chelate formed is positively charged and is complexed to a hydroxide complex ion.

12. A method as in claim 1 wherein a minor amount of water is added to the particulate blend to drive the reaction toward completion.

13. A method as in claim 1 wherein said metal amino acid chelate has a ligand to metal molar ratio of about 2:1 and the reaction is further defined by:

$$Ca(OH)_2 + 2H(AA) + MSO_4 \cdot nH_2O \rightarrow$$
$$M(AA)_2 + CaSO_4 + (n+1)H_2O$$

where H(AA) is one or more naturally occurring amino acids; H when disassociated from AA is a hydrogen ion donor from the carboxyl group present on the amino acid; M is selected from the group consisting of Cu, Zn, Fe, Co, Mg, Mn, and combinations thereof; and n is an integer from about 1 to 15.

14. A method as in claim 1 wherein said metal amino acid chelate has a ligand to metal molar ratio of about 2:1 and the reaction is further defined by:

$$CaO + 2H(AA) + MSO_4 \cdot nH_2O \rightarrow$$
$$M(AA)_2 + CaSO_4 + (n+1)H_2O$$

where H(AA) is one or more naturally occurring amino acids; H when disassociated from AA is a hydrogen ion donor from the carboxyl group present on the amino acid; M is selected from the group consisting of Cu, Zn, Fe, Co, Mg, Mn, and combinations thereof; and n is an integer from about 1 to 15.

15. A method as in claim 1 wherein said metal amino acid chelate has a ligand to metal molar ratio of about 3:1 and the reaction is further defined by:

$$3Ca(OH)_2 + 6H(AA) + M'_2(SO_4)_3 \cdot nH_2O \rightarrow$$
$$2M'(AA)_3 + 3CaSO_4 + (n+6)H_2O$$

where H(AA) is one or more naturally occurring amino acids; H when disassociated from AA is a hydrogen ion donor from the carboxyl group present on the amino acid; M' is selected from the group consisting of Fe, Cr, Mo, and combinations thereof; and n is an integer from about 1 to 15.

16. A method as in claim 1 wherein said metal amino acid chelate has a ligand to metal molar ratio of about 3:1 and the reaction is further defined by:

$$3CaO + 6H(AA) + M'_2(SO_4)_3 \cdot nH_2O \rightarrow$$
$$2M'(AA)_3 + 3CaSO_4 + (n+3)H_2O$$

where H(AA) is one or more naturally occurring amino acids; H when disassociated from AA is a hydrogen ion donor from the carboxyl group present on the amino acid; M' is selected from the group consisting of Fe, Cr, Mo, and combinations thereof; and n is an integer from about 1 to 15.

17. A method as in claim 1 wherein said metal amino acid chelate has a ligand to metal molar ratio of about 1:1 and the reaction is further defined by:

$$Ca(OH)_2 H(AA) + MSO_4 \cdot nH_2O \rightarrow$$
$$M'(AA)^+OH^- + CaSO_4 + (n+1)H_2O$$

where H(AA) is one or more naturally occurring amino acids; H when disassociated from AA is a hydrogen ion donor from the carboxyl group present on the amino acid; M is selected from the group consisting of Cu, Zn, Fe, Co, Mg, Mn, and combinations thereof; and n is an integer from about 1 to 15.

18. A method as in claim 1 wherein said metal amino acid chelate has a ligand to metal molar ratio of about 1:1 and the reaction is further defined by:

$$CaO + H(AA) + MSO_4 \cdot nH_2O \rightarrow$$
$$M(AA)^+OH^- + CaSO_4 + nH_2O$$

where H(AA) is one or more naturally occurring amino acids; H when disassociated from AA is a hydrogen ion donor from the carboxyl group present on the amino acid; M is selected from the group consisting of Cu, Zn, Fe, Co, Mg, Mn, and combinations thereof; and n is an integer from about 1 to 15.

19. A method as in claim 1 wherein said metal amino acid chelate has a ligand to metal molar ratio of about 2:1 and the reaction is further defined by:

$$3Ca(OH)_2 + 4H(AA) + M'_2(SO_4)_3 \cdot nH_2O \rightarrow$$
$$2[M'(AA)_2^+OH^-] + 3CaSO_4 + (n+4)H_2O$$

where H(AA) is one or more naturally occurring amino acids; H when disassociated from AA is a hydrogen ion donor from the carboxyl group present on the amino acid; M' is selected from the group consisting of Fe, Cr, Mo, and combinations thereof; and n is an integer from about 1 to 15.

20. A method as in claim 1 wherein said metal amino acid chelate has a ligand to metal molar ratio of about 2:1 and the reaction is further defined by:

$$3CaO + 4H(AA) + M'_2(SO_4)_3 \cdot nH_2O \rightarrow$$
$$2[M'(AA)_2^+OH^-] + 3CaSO_4 + (n+1)H_2O$$

where H(AA) is one or more naturally occurring amino acids; H when disassociated from AA is a hydrogen ion donor from the carboxyl group present on the amino acid; M' is selected from the group consisting of Fe, Cr, Mo, and combinations thereof; and n is an integer from about 1 to 15.

21. Particulate amino acid chelates and complexes essentially free of interfering complex ions prepared by:
  a) combining as a particulate blend
    i) a hydrated metal sulfate salt having one or more waters of hydration,
    ii) an amino acid ligand, and
    iii) calcium oxide or hydroxide,
  at a ratio sufficient to allow substantially all of the particulates to react forming a metal amino acid chelate, calcium sulfate, residual water, and optionally, a hydroxide complex ion, and wherein the metal amino acid chelate has a ligand to metal molar ratio from about 1:1 to 3:1;
  b) placing the particulate blend in an enclosed environment; and
  c) applying heat to the particulate blend in the enclosed environment causing the waters of hydration of the hydrated metal sulfate salt to be released into the enclosed environment thereby causing a reaction resulting in the formation of a metal amino acid chelate or complex and calcium sulfate.

22. Particulate amino acid chelates and complexes as in claim 21 wherein said amino acid ligand is selected from the group consisting of alanine, arginine, asparagine, aspartic acid, cysteine, cystine, glutamine, glutamic acid, glycine, histidine, hydroxyproline, isoleucine, leucine, lysine, methionine, ornithine, phenylalanine, proline, serine, threonine, tryptophan, tyrosine, valine, and combinations thereof, and dipeptides, tripeptides, and tetrapeptides formed by any combination of said amino acids thereof.

23. Particulate amino acid chelates and complexes as in claim 21 wherein said metal sulfate salt is selected from the group consisting of iron sulfate hydrates, copper sulfate hydrates, zinc sulfate hydrates, manganese sulfate hydrates, cobalt sulfate hydrates, magnesium sulfate hydrates, chromium sulfate hydrates, molybdenum sulfate hydrates, and combinations thereof.

24. Particulate amino acid chelates and complexes as in claim 21 wherein the particulate blend within the enclosed environment is heated at temperatures from about 50° C. to 100° C.

25. Particulate amino acid chelates and complexes as in claim 21 wherein following the heating step, the temperature of the particulate blend is reduced to room temperature and allowed to continue to react.

26. Particulate amino acid chelates and complexes as in claim 22 wherein the amino acid ligand is glycine.

27. Particulate amino acid chelates and complexes as in claim 22 wherein the amino acid ligand is comprised of glycine and at least one of the other naturally occurring amino acids.

28. Particulate amino acid chelates and complexes as in claim 23 wherein the hydrated metal sulfate salt is selected from the group consisting of ferrous sulfate tetrahydrate, ferrous sulfate heptahydrate, copper sulfate pentahydrate, manganese sulfate pentahydrate, zinc sulfate pentahydrate, magnesium sulfate nonahydrate, chromium sulfate heptahydrate, zinc sulfate monohydrate, and combinations thereof.

29. Particulate amino acid chelates and complexes as in claim 21 further comprising a preliminary step of grinding said ligand and said hydrated metal sulfate salt into a powder from about 20 to 80 mesh.

30. Particulate amino acid chelates and complexes as in claim 21 wherein the amino acid chelate formed is electrically neutral.

31. Particulate amino acid chelates and complexes as in claim 21 wherein the amino acid chelate formed is positively charged and is complexed to a hydroxide complex ion.

32. Particulate amino acid chelates and complexes as in claim 21 wherein a minor amount of water is added to the particulate blend to drive the reaction toward completion.

33. Particulate amino acid chelates and complexes as in claim 21 wherein said metal amino acid chelate has a ligand to metal molar ratio of about 2:1 and the reaction is further defined by:

$$Ca(OH)_2 + 2H(AA) + MSO_4 \cdot nH_2O \rightarrow$$

$$M(AA)_2 + CaSO_4 + (n+2)H_2O$$

where H(AA) is one or more naturally occurring amino acids; H when disassociated from AA is a hydrogen ion donor from the carboxyl group present on the amino acid; M is selected from the group consisting of Cu, Zn, Fe, Co, Mg, Mn, and combinations thereof; and n is an integer from about 1 to 15.

34. Particulate amino acid chelates and complexes as in claim 21 wherein said metal amino acid chelate has a ligand to metal molar ratio of about 2:1 and the reaction is further defined by:

$$CaO + 2H(AA) + MSO_4 \cdot nH_2O \rightarrow$$

$$M(AA)_2 + CaSO_4 + (n+1)H_2O$$

where H(AA) is one or more naturally occurring amino acids; H when disassociated from AA is a hydrogen ion donor from the carboxyl group present on the amino acid; M is selected from the group consisting of Cu, Zn, Fe, Co, Mg, Mn, and combinations thereof; and n is an integer from about 1 to 15.

35. Particulate amino acid chelates and complexes as in claim 21 wherein said metal amino acid chelate has a ligand to metal molar ratio of about 3:1 and the reaction is further defined by:

$$3Ca(OH)_2 + 6H(AA) + M'_2(SO_4)_3 \cdot nH_2O \rightarrow$$

$$2M'(AA)_2 + 3CaSO_4 + (n+6)H_2O$$

where H(AA) is one or more naturally occurring amino acids; H when disassociated from AA is a hydrogen ion donor from the carboxyl group present on the amino acid; M' is selected from the group consisting of Fe, Cr, Mo, and combinations thereof; and n is an integer from about 1 to 15.

36. Particulate amino acid chelates and complexes as in claim 21 wherein said metal amino acid chelate has a ligand to metal molar ratio of about 3:1 and the reaction is further defined by:

$$3CaO + 6H(AA) + M'_2(SO_4)_3 \cdot nH_2O \rightarrow$$

$$2M'(AA)_3 + 3CaSO_4 + (n+3)H_2O$$

where H(AA) is one or more naturally occurring amino acids; H when disassociated from AA is a hydrogen ion donor from the carboxyl group present on the amino acid; M' is selected from the group consisting of Fe, Cr, Mo, and combinations thereof; and n is an integer from about 1 to 15.

37. Particulate amino acid chelates and complexes as in claim 21 wherein said metal amino acid chelate has a ligand to metal molar ratio of about 1:1 and the reaction is further defined by:

$$Ca(OH)_2 + H(AA) + MSO_4 \cdot nH_2O \rightarrow$$

$$M(AA)^+OH^- + CaSO_4 + (n+1)H_2O$$

where H(AA) is one or more naturally occurring amino acids; H when disassociated from AA is a hydrogen ion donor from the carboxyl group present on the amino acid; M is selected from the group consisting of Cu, Zn, Fe, Co, Mg, Mn, and combinations thereof; and n is an integer from about 1 to 15.

38. Particulate amino acid chelates and complexes as in claim 21 wherein said metal amino acid chelate has a ligand to metal molar ratio of about 1:1 and the reaction is further defined by:

$$CaO + H(AA) + MSO_4 \cdot nH_2O \rightarrow$$

$$M(AA)^+OH^- + CaSO_4 + nH_2O$$

where H(AA) is one or more naturally occurring amino acids; H when disassociated from AA is a hydrogen ion donor from the carboxyl group present on the amino acid; M is selected from the group consisting of Cu, Zn, Fe, Co, Mg, Mn, and combinations thereof; and n is an integer from about 1 to 15.

39. Particulate amino acid chelates and complexes as in claim 21 wherein said metal amino acid chelate has a ligand to metal molar ratio of about 2:1 and the reaction is further defined by:

$$3Ca(OH)_2 + 4H(AA) + M'_2(SO_4)_3 \cdot nH_2O \rightarrow$$
$$2[M'(AA)_2^{+OH^-}] + 3CaSO_4 + (n+4)H_2O$$

where H(AA) is one or more naturally occurring amino acids; H when disassociated from AA is a hydrogen ion donor from the carboxyl group present on the amino acid; M' is selected from the group consisting of Fe, Cr, Mo, and combinations thereof; and n is an integer from about 1 to 15.

40. Particulate amino acid chelates and complexes as in claim 21 wherein said metal amino acid chelate has a ligand to metal molar ratio of about 2:1 and the reaction is further defined by:

$$3CaO + 4H(AA) + M'_2(SO_4)_3 \cdot nH_2O \rightarrow$$
$$2[M'(AA)_2^{+OH^-}] + 3CaSO_4 + (n+1)H_2O$$

where H(AA) is one or more naturally occurring amino acids; H when disassociated from AA is a hydrogen ion donor from the carboxyl group present on the amino acid; M' is selected from the group consisting of Fe, Cr, Mo, and combinations thereof; and n is an integer from about 1 to 15.

* * * * *